United States Patent
Palmer et al.

(10) Patent No.: US 8,921,813 B2
(45) Date of Patent: Dec. 30, 2014

(54) REFLECTOR FOR ULTRAVIOLET STERILIZER FIXTURE

(71) Applicants: William Palmer, Amsterdam, NY (US); Joseph M. Cattadoris, Jr., Amsterdam, NY (US)

(72) Inventors: William Palmer, Amsterdam, NY (US); Joseph M. Cattadoris, Jr., Amsterdam, NY (US)

(73) Assignee: William Palmer, Amsterdam, NY (US)

( * ) Notice: Subject to any disclaimer, the term of this patent is extended or adjusted under 35 U.S.C. 154(b) by 186 days.

(21) Appl. No.: 13/625,198

(22) Filed: Sep. 24, 2012

(65) Prior Publication Data

US 2014/0084185 A1   Mar. 27, 2014

(51) Int. Cl.
*A61L 2/10* (2006.01)
*A61L 9/20* (2006.01)
*A61N 5/06* (2006.01)
*F21V 7/06* (2006.01)
*H01J 61/02* (2006.01)
*F21V 7/00* (2006.01)

(52) U.S. Cl.
CPC ... *A61L 2/10* (2013.01); *A61L 9/20* (2013.01); *H01J 61/025* (2013.01); *F21V 7/005* (2013.01); *A61N 5/0624* (2013.01)

USPC .................................................. 250/504 R

(58) Field of Classification Search
CPC .......... A61L 9/20; A61L 2/10; A61N 5/0624; F21V 7/005; H01J 61/025
USPC .................................................. 250/504 R
See application file for complete search history.

(56) References Cited

U.S. PATENT DOCUMENTS

| | | | |
|---|---|---|---|
| 2,418,195 A | | 4/1947 | Rolph |
| 2,569,772 A | * | 10/1951 | Olsen ................. 362/217.03 |
| 4,596,935 A | * | 6/1986 | Lumpp ................. 250/495.1 |
| 6,457,846 B2 | * | 10/2002 | Cook et al. ................. 362/321 |
| 8,162,504 B2 | | 4/2012 | Zhang et al. |

* cited by examiner

*Primary Examiner* — Jack Berman
(74) *Attorney, Agent, or Firm* — David L. Nocilly; Bond Schoeneck & King, PLLC

(57) ABSTRACT

An ultraviolet (UV) germicidal or sterilization fixture having a dual parabolic reflecting assembly for collimating and redirecting UV light. The first pair of parabolic reflectors are positioned to collimate and reflect light emanating from the sides of the UV light source and spaced apart proximately to the rear surface of the UV source to allow light to pass through. The second pair of reflectors are positioned behind the first pair and aligned to capture light passing through the gap formed by the first pair of reflectors and then collimate and redirect the light produced by the rear of the light source out of the front of the fixture.

9 Claims, 8 Drawing Sheets

REFLECTOR FOR ULTRAVIOLET STERILIZER FIXTURE

BACKGROUND OF THE INVENTION

1. Field of the Invention

The present invention relates to ultraviolet germicidal fixtures and, more particularly, to a reflector that increases the amount of available ultraviolet light.

2. Description of the Related Art

Health concerns over certain diseases, such as tuberculosis, have increased efforts to prevent transmission of infections that are completely or partially airborne using environmental system. One such system, ultraviolet germicidal irradiation, involves the use of UV lamps, such as low-pressure mercury (Hg) discharge lamps, to emit shortwave ultraviolet-C radiation that kills or inactivates microbes in the air. Air disinfection is typically accomplished by using a UV light fixture that irradiates only the upper-room air, thereby protecting the occupants of the room from harmful radiation while sterilizing the upper air in room. These fixtures are generally wall-mounted or ceiling-suspended, and include louvers or shields to confine the germicidal radiation to the entire room area above any occupants. Although effective air disinfection depends, in part, on good vertical air movement, the efficiency of such systems are largely dependent on the amount of UV light generated by the fixture. Accordingly, there is a need in the art to improve the efficiency and amount of effective UV radiation provided by upper air fixtures to ensure adequate germicidal functioning and to reduce overall system costs.

BRIEF SUMMARY OF THE INVENTION

The present invention comprises an ultraviolet (UV) germicidal or sterilization fixture having a dual parabolic reflecting assembly for collimating and redirecting a high percentage of UV light from a UV light source out of the fixture. The reflecting assembly includes a first pair of parabolic reflectors positioned to collimate and reflect light emanating from the sides, i.e., the top and bottom, an elongated UV light source. The first pair of reflectors are spaced apart proximate to the rear surface of the UV source to allow light emanating from the rear surface of the UV source to pass through. The reflecting assembly includes a second pair of reflectors positioned behind the first pair and aligned to capture light passing through the gap formed by the first pair of reflectors at the rear surface of the light source. The second pair of reflectors include sequential parabolic and planar portions oriented to collimate and capture the light produced by the rear of the light source and redirect the light out of the front of the fixture.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION OF THE INVENTION

Figure 1:
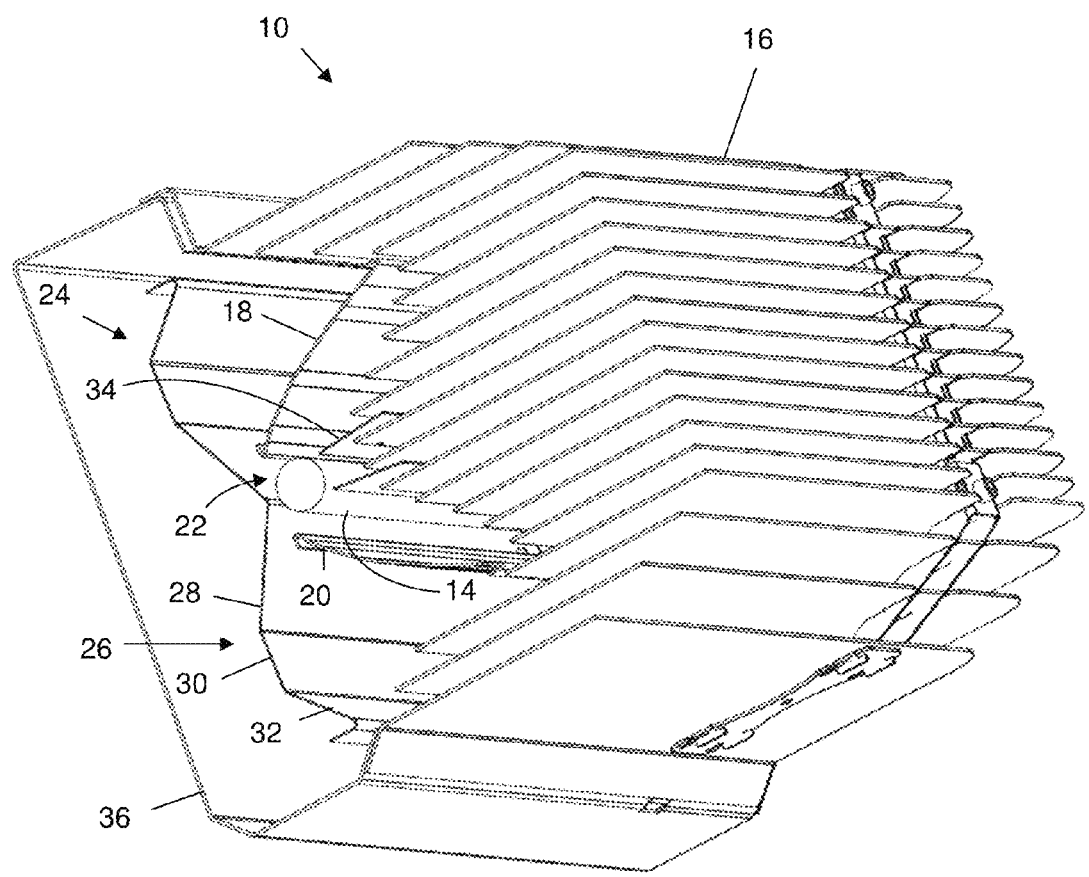
FIG. 1 is a cross-sectional view of a UV sterilizer fixture according to the present invention.
Figure 2:
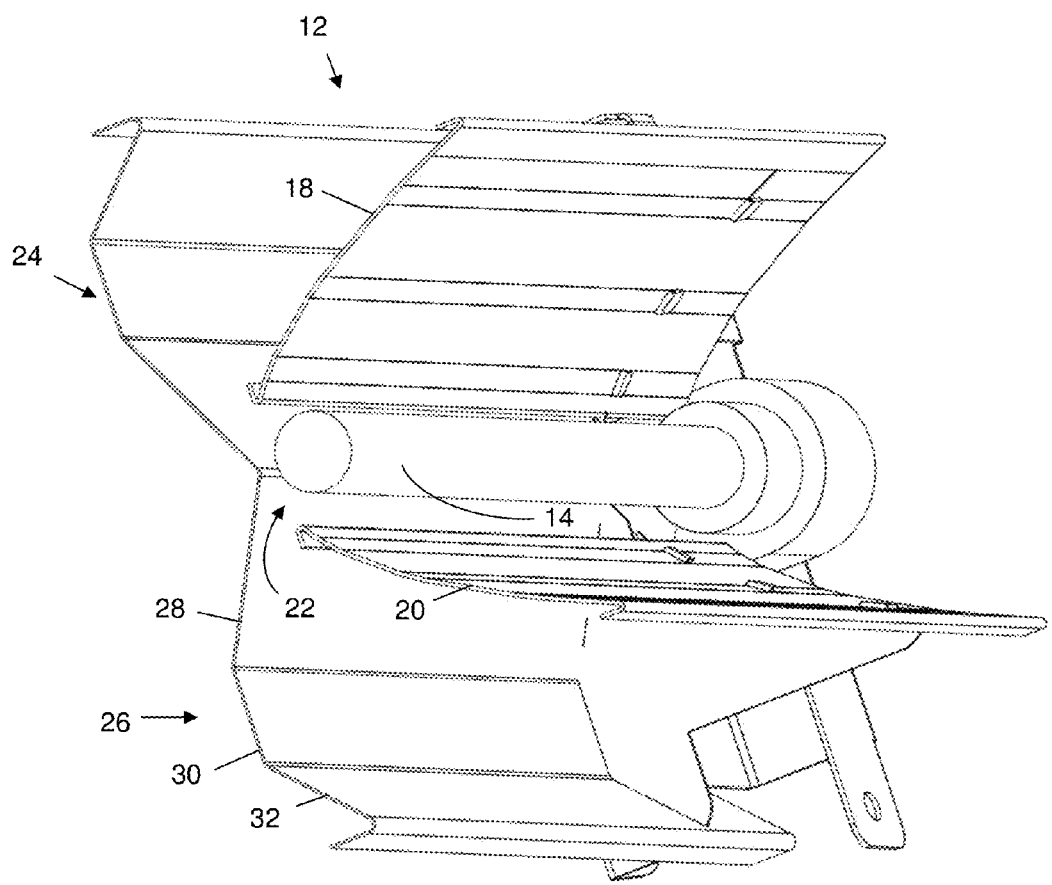
FIG. 2 is a cross-sectional view of a reflector assembly for a UV sterilizer fixture according to the present invention.

Referring now to the drawings, wherein like reference numerals refer to like parts throughout, there is seen in FIGS. 1 and 2 an ultraviolet (UV) sterilizer fixture 10 according to the present invention. Fixture 10 comprises a reflector assembly 12, a UV light source 14 positioned in front of reflector assembly 12, and a set of baffles 16 for controlling the direction of UV light emanating from fixture 10. Baffles 16 ensure that UV light extends laterally from fixture 10, thereby protecting against the undesired exposure of occupants of a room to UV light when fixture is positioned to sterilize just the upper air in the room. UV light source 14 may comprise any conventional elongated or linear UVC light bulb or tube for germicidal application. As will be explained below, reflector assembly 12 improves the amount of available UV light reflected outwardly from fixture 10 and improves the collimation of UV light emitted from fixture 10.

Referring to FIG. 2, reflector 12 comprises a first pair of opposing reflectors 18 and 20 positioned on above and below an elongated light source 14. Preferably, reflectors 18 and 20 are spaced apart from each other directly opposite the rear surface of light source 14, thereby forming a gap 22 for permitting UV light produced by light source 14 to pass therethrough. As further seen in FIG. 1, reflector assembly 12 further comprises a second pair of opposing reflectors 24 and 26 positioned behind first pair of reflectors 18 and 20. Reflectors 24 and 26 are preferably connected at a point directly proximate to gap 22 formed by reflectors 18 and 20, thereby collecting UV light emanating from the rear of light source 14 and passing through gap 22 and directing the UV light forwardly out of fixture 10.

Figure 3:
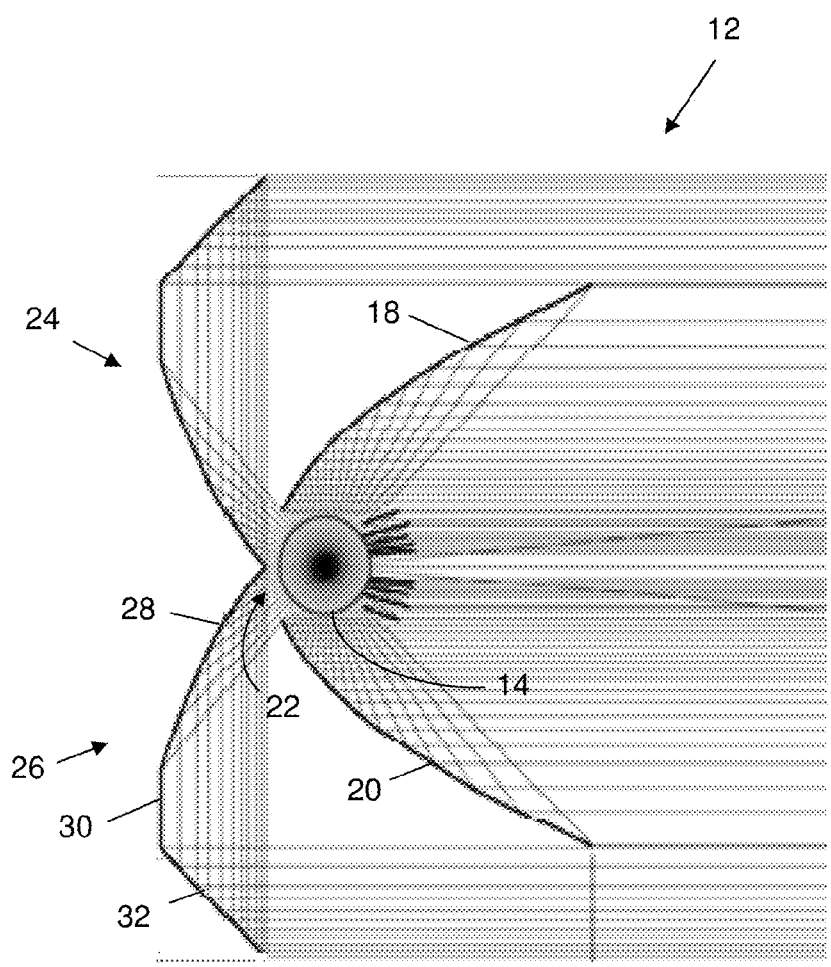
FIG. 3 is a schematic of light rays reflected by a reflector assembly according to the present invention.

As seen in FIG. 3, reflectors 18 and 20 are preferably parabolic in geometry, thereby directing light emanating from the sides of light source 14 outwardly from fixture 10 in a collimated fashion. As further seen in FIG. 2, reflectors 24 and 26 are generally parabolic to collimate and redirect light passing through gap 22 so that it can be redirected to pass outwardly from fixture 10. Preferably, each of reflectors 24 and 26 include a parabolic portion 28 immediately opposite gap 22 to capture and collimate light passing through gap 22, a first planar portion 30 extending from parabolic portion 28, and a second planar portion 32 extending from first planar portion 30 and oriented to reflect collimated light received from parabolic portion 28 outwardly from fixture 10. Fixture 10 may further include one or more forward reflectors 34 in front of light source 14 to direct light as desired. The various reflectors of reflector assembly 12 are preferably manufactured from anodized, highly-reflective aluminum and preferably rated to reflect up to 100 percent of ultraviolet light. For example, the 4300 UP material available from Alanod, GmbH of Ennepetal, Germany may be used to manufacture reflector assembly 12.

Figure 4:
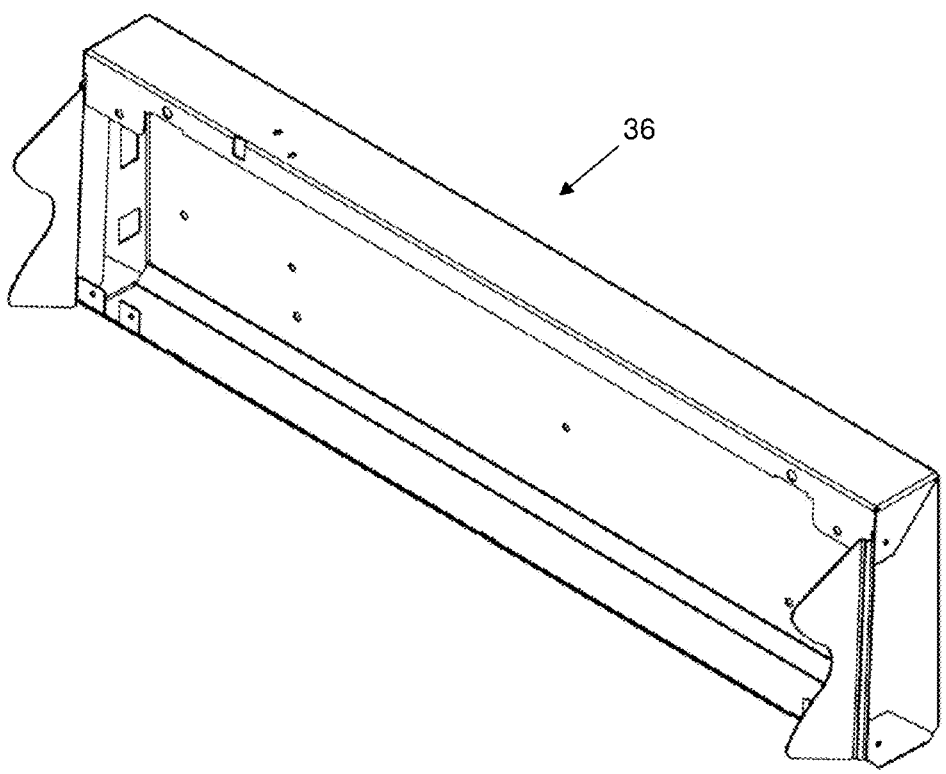
FIG. 4 is a perspective view of a ballast housing for a UV sterilizer fixture according to the present invention.
Figure 5:
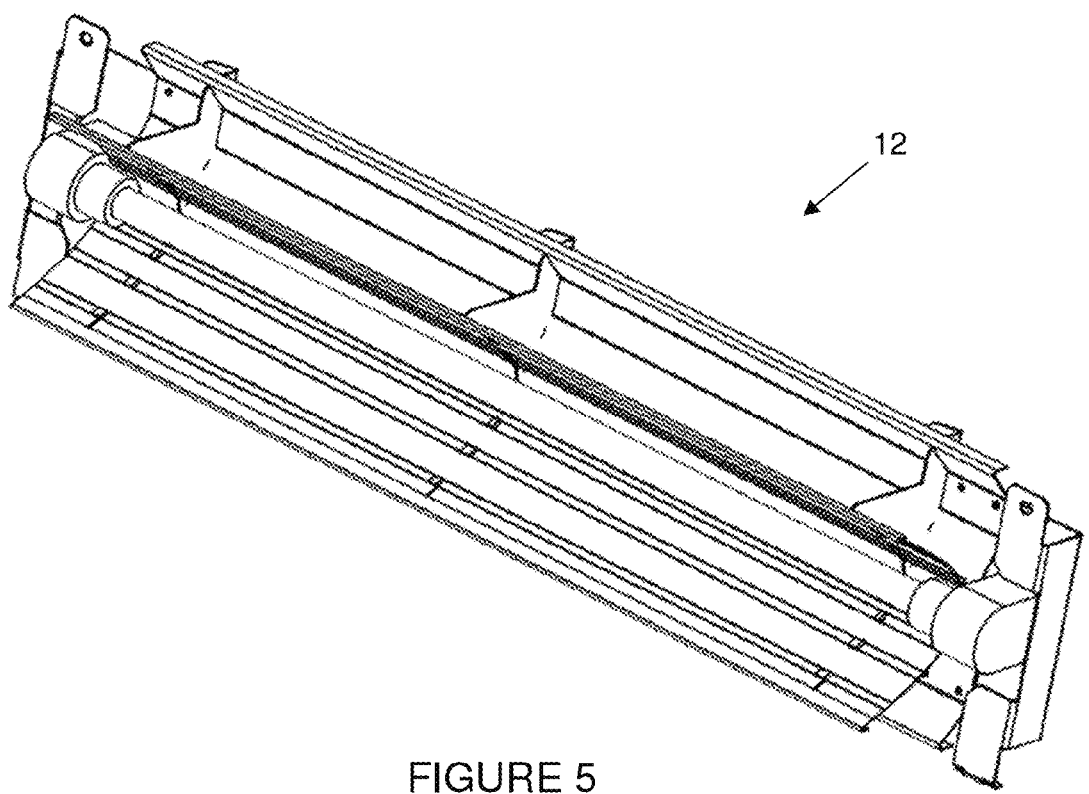
FIG. 5 is a perspective view of a reflector assembly for a UV sterilizer fixture according to the present invention.
Figure 6:
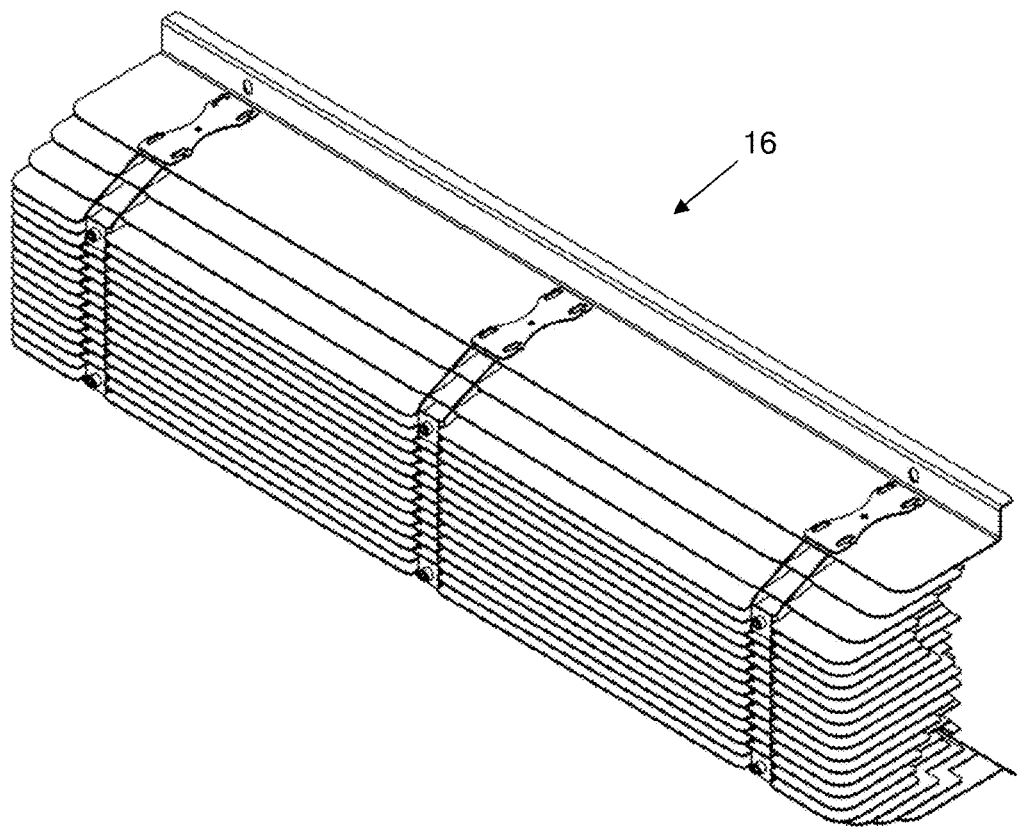
FIG. 6 is a perspective view of a baffle assembly for a UV sterilizer fixture according to the present invention.
Figure 7:
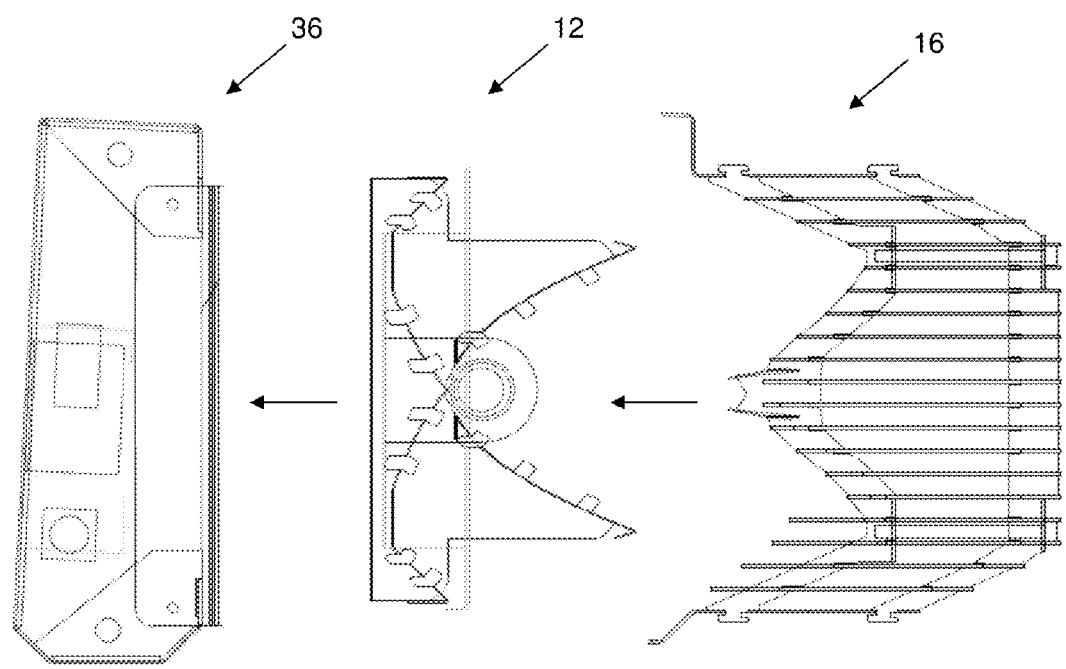
FIG. 7 is a cross-sectional, exploded view showing the interconnection of a ballast housing, reflector assembly, and baffle assembly according to the present invention.
Figure 8:
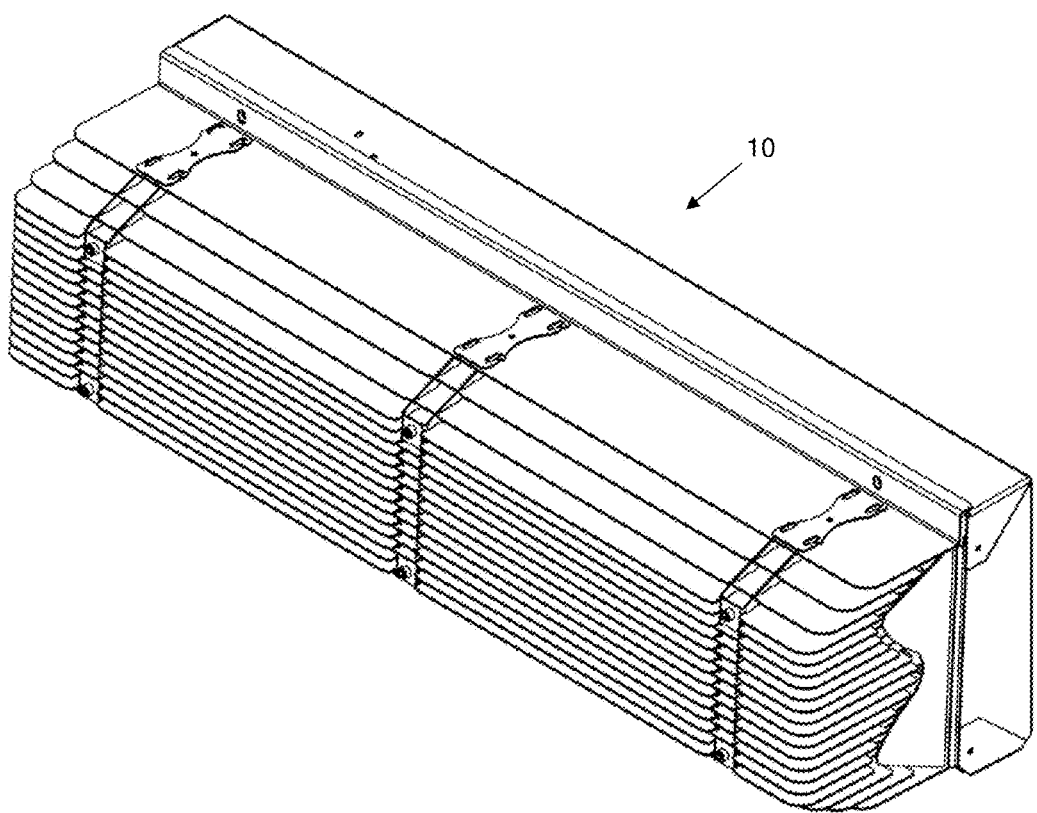
FIG. 8 is a perspective view of an assembled UV sterilizer fixture according to the present invention.

Referring to FIG. 4-6, fixture 10 may further comprise a ballast housing 36 that may be interconnected to and support reflector assembly 12 and baffles 16, and electrically interconnected to light source 14 to provide electrical power. As seen in FIG. 7, assembly of fixture 10 involves attaching reflector assembly 12 to ballast housing 36, and then positioning baffles 16 over reflector assembly 12. An electrical ballast (not shown) that is positioned in housing 36 and electrically interconnected to light source 14 may comprise any conventional ballast specified for use in connection with a UVC lamp bulb.

EXAMPLE

UV light produced by a fixture having a reflecting assembly according to the present invention was tested and compared to UV light produced by a conventional, off-the-shelf fixture. As seen in the results compiled in Table 1 (single parabolic reflector) and Table 2 (present invention) below, the present invention produced a significantly higher amount of UV light at various distances from the fixture. Measurements were taken with a ceiling height of ten feet, an angle from the fixture of 90 degrees and an installed height of seven feet.

TABLE 1

UV output of conventional reflector fixture

| Height | Distance | | | | | | |
|---|---|---|---|---|---|---|---|
|  | 36" | 60" | 84" | 108" | 132" | 156" | 180" |
| 108" | .77 | 3.1 | 4.4 | 4.4 | 8 | 10.5 | 10.9 |
| 105" | 1.7 | 5.3 | 6 | 10 | 14.32 | 15 | 13.64 |
| 102" | 4 | 8.6 | 12.54 | 21 | 21.41 | 18.78 | 15.56 |
| 101" | 5.2 | 10 | 19.02 | 25.3 | 23.7 | 20.17 | 15.49 |
| 100" | 14.93 | 20.51 | 25.7 | 29.3 | 25.5 | 11.7 | 7.1 |
| 99" | 10.5 | 15.49 | 33.6 | 33.8 | 27.7 | 20.1 | 14.02 |
| 98" | 13.75 | 27 | 44.1 | 38.2 | 28.4 | 19.08 | 13.3 |
| 97" | 18.93 | 44.9 | 53 | 41.6 | 27.9 | 18.24 | 12.68 |
| 96" | 24.7 | 66.6 | 62.7 | 42.6 | 26.1 | 16.96 | 11.7 |
| 95" | 38.2 | 94.6 | 69 | 40.3 | 24 | 15.39 | 10.5 |
| 94" | 88.2 | 120.4 | 69.2 | 36.9 | 21.6 | 14 | 9.9 |
| 93" | 177.4 | 133.6 | 62.7 | 32.4 | 19.22 | 12.53 | 8.8 |
| 92" | 306 | 127.7 | 53.7 | 28.1 | 16.68 | 11.2 | 7.9 |
| 91" | 351 | 103.8 | 42.8 | 23.2 | 14.43 | 9.7 | 7.3 |
| 90" | 283 | 79 | 34.3 | 19.44 | 12.3 | 8.4 | 6.1 |
| 89" | 156.7 | 52.1 | 25.3 | 14.9 | 9.8 | 6.9 | 5.2 |
| 88" | 73.3 | 27.1 | 15.17 | 10.1 | 7.2 | 5.3 | 4.2 |
| 87" | 27.8 | 12.87 | 8.2 | 6.3 | 5 | 4 | 3.3 |
| 86" | 21.91 | 9.8 | 5 | 3.4 | 2.9 | 2.5 | 2.3 |
| 85" | 16.31 |  |  |  |  |  |  |
| 84" | 13.48 | 8.1 | 4.7 | 3 | 2 | 1.5 | 1.2 |

TABLE 2

UV output of present invention

| Height | Distance | | | | | | |
|---|---|---|---|---|---|---|---|
|  | 36" | 60" | 84" | 108" | 132" | 156" | 180" |
| 108" |  |  |  |  | .82 | 4.5 | 8.3 |
| 105" |  |  |  | 1.8 | 7.5 | 14.05 | 15.01 |
| 102" |  | .32 | 2.2 | 9.7 | 20.6 | 22.9 | 21.5 |
| 101" |  |  |  | 25.1 | 25.8 | 23.6 |  |
| 100" |  |  |  | 25.2 | 31.4 | 29.4 | 26.2 |
| 99" | 2.7 | 2 | 14.96 | 34 | 35.5 | 32.3 | 27.7 |
| 98" | 2.3 | 7.8 | 27.2 | 43.5 | 40.3 | 35.3 | 28.7 |
| 97" | 2.8 | 16.31 | 45.4 | 52.7 | 45.6 | 37.8 | 29.2 |
| 96" | 4.1 | 23.2 | 63.3 | 60.3 | 50.1 | 38.6 | 29.2 |
| 95" | 8 | 49.3 | 82.3 | 67.4 | 52.1 | 37.4 | 27.9 |
| 94" | 27.5 | 96.4 | 99 | 73.8 | 51.9 | 37 | 26.4 |
| 93" | 63.1 | 159.1 | 117.4 | 79.8 | 53.3 | 35.6 | 24.6 |
| 92" | 151.2 | 194.7 | 121.2 | 77.1 | 48.1 | 32.1 | 22.7 |
| 91" | 298 | 218 | 126.1 | 74.6 | 44.7 | 29 | 20.5 |
| 90" | 424 | 223 | 115.6 | 64.4 | 39.3 | 25.9 | 18.5 |
| 89" | 473 | 221 | 103.4 | 56.4 | 34.8 | 22.7 | 16.33 |
| 88" | 441 | 183.3 | 81.7 | 46.2 | 29.6 | 20.2 | 14.83 |

TABLE 2-continued

UV output of present invention

| Height | Distance | | | | | | |
|---|---|---|---|---|---|---|---|
|  | 36" | 60" | 84" | 108" | 132" | 156" | 180" |
| 87" | 329 | 117.1 | 61.7 | 37.8 | 24.7 | 17.44 | 13.02 |
| 86" | 160.5 | 68.2 | 40.7 | 27.1 | 19.26 | 14.1 | 10.7 |
| 85" | 61.3 | 34.2 | 24.2 | 19.15 | 14.6 | 10.9 | 8.8 |
| 84" | 16.2 | 14.09 | 11.8 | 10.4 | 9.2 | 7.7 | 7 |

The present invention thus increases performance while allowing the use of standard components. This increase in output may allow a user to install fewer units and still create the necessary irradiance levels throughout a given space. These advantages will reduce the cost of the initial installation while also reducing the cost of maintain and powering the equipment.

What is claimed is:

1. A germicidal ultraviolet light fixture, comprising:
an ultraviolet light source for emitting ultraviolet light;
a first pair of reflectors positioned on either side of said light source to reflect light from said light source in a first predetermined direction and spaced apart relative to each other to form a gap that will permit light from said light source to pass in a second predetermined direction, wherein each of said first pair of reflectors is parabolic and positioned so that light emitted from said light source and reflected by said first pair of reflectors is collimated and reflected into said first predetermined direction; and
a second pair of reflectors positioned behind said first pair of reflectors and positioned to reflect light emitted from said light source in said second predetermined direction to said first predetermined direction, wherein each of said second pair of reflectors includes a parabolic portion positioned so that light emitted from said light source in said second predetermined direction is collimated and reflected into a third predetermined direction.

2. The fixture of claim 1, wherein each of said second pair of reflectors includes a planar portion for reflecting light that had been collimated and reflected by said parabolic portion in said third predetermined direction into said first predetermined direction.

3. The fixture of claim 2, wherein each of said second pair of reflectors includes a second planar portion interconnecting said first planar portion and parabolic portion and spacing said first planar portion outwardly beyond said first pair of reflectors.

4. The fixture of claim 3, further comprising a third set of reflectors positioned in front of said light source to collimate light emitting from the front of said light source.

5. The fixture of claim 4, further comprising a set of baffles positioned in front of said light source.

6. A method of improving the performance of an ultraviolet germicidal fixture, comprising the steps of:
providing an ultraviolet light source for emitting ultraviolet light;
reflecting light emitted from said light source in a first predetermined direction;
allowing a portion of light emitted from said light source to pass in a second predetermined direction;
reflecting light passing in said second predetermined direction into a third predetermined direction; and
reflecting light passing in said third predetermined direction into said first predetermined direction.

7. The method of claim 6, wherein the step of reflecting light emitted from said light source in a first predetermined direction comprises collimating and reflecting light with a first pair of parabolic reflectors that are spaced apart proximately to said light source to form a gap therebetween.

8. The method of claim 7, wherein the step of reflecting light passing in said second predetermined direction into a third predetermined direction comprises reflecting light with a second pair of reflectors, each of which includes a parabolic portion positioned proximately to said gap.

9. The method of claim 8, wherein the step of reflecting light passing in said third predetermined direction into said first predetermined direction comprises reflecting light with said second pair of reflectors, wherein each of said second pair of reflectors further includes a planar portion positioned to reflect light passing in said third predetermined direction into said first predetermined direction.

\* \* \* \* \*